United States Patent

Phaff

Patent Number: 5,097,044
Date of Patent: Mar. 17, 1992

[54] PYRAN-CONTAINING PHTHALIDES

[75] Inventor: Rox Phaff, Itingen, Switzerland

[73] Assignee: Ciba-Geigy Corporation, Ardsley, N.Y.

[21] Appl. No.: 585,745

[22] Filed: Sep. 20, 1990

[30] Foreign Application Priority Data

Sep. 27, 1989 [CH] Switzerland ............ 3497/89

[51] Int. Cl.$^5$ ............... C07D 307/77; C07D 311/04
[52] U.S. Cl. ................. 549;307; 549/310; 549/398; 549/226; 549/265; 548/510; 546/89; 546/116; 544/345; 544/350; 503/220
[58] Field of Search ......... 549/307, 310, 398, 226, 549/265; 503/220; 546/89, 116; 544/345, 350; 548/510

[56] References Cited

U.S. PATENT DOCUMENTS 4,876,357  10/1989  Phaff et al. .......... 548/463

FOREIGN PATENT DOCUMENTS 0266310  5/1988  European Pat. Off. .

Primary Examiner—Glennon H. Hollrah
Assistant Examiner—Shailendra Kumar
Attorney, Agent, or Firm—George R. Dohmann; Marla Mathias

[57] ABSTRACT

Pyran-containing phthalides of the formula

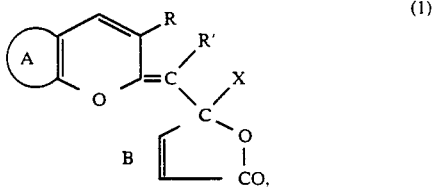

in which

R is hydrogen, alkyl which has not more than 12 carbon atoms and is unsubstituted or substituted by halogen, cyano, hydroxyl or lower alkoxy, or is cycloalkyl, phenalkyl or phenyl each of which is unsubstituted or substituted, or an unsubstituted or substituted heterocyclic radical, R' is hydrogen, or R together with R' is $C_2$–$C_3$alkylene which is unsubstituted or substituted by methyl, X is hydrogen, alkyl having 1 to 12 carbon atoms or a monocyclic or polycyclic aromatic or heteroaromatic radical and the ring A is a benzene or naphthalene ring which is unsubstituted or monosubstituted or polysubstituted by halogen, lower alkyl, lower alkoxy or lower alkoxycarbonyl, and the ring B is an aromatic or heteroaromatic radical which has 6 ring atoms and which can contain an aromatic fused ring, it being possible for both the ring B and the fused ring to be substituted.

These phthalides are particularly suitable for use as color-formers in pressure-sensitive or heat-sensitive recording materials and produce light-fast, orange, red, violet, green-blue, blue or violet-blue color shades.

8 Claims, No Drawings

PYRAN-CONTAINING PHTHALIDES

The present invention relates to pyran-containing phthalides, to a process for their preparation and to their use as colour-formers in pressure-sensitive or heat-sensitive recording materials.

The phthalides according to the invention have the general formula

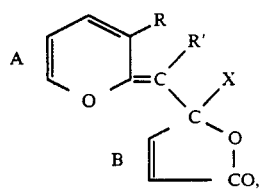
(1)

in which

R is hydrogen, alkyl which has not more than 12 carbon atoms and is unsubstituted or substituted by halogen, cyano, hydroxyl or lower alkoxy, or is cycloalkyl, phenalkyl or phenyl each of which is unsubstituted or substituted, or an unsubstituted or substituted heterocyclic radical, R' is hydrogen, or R together with R' is $C_2$-$C_3$alkylene which is unsubstituted or substituted by methyl, X is hydrogen, alkyl having 1 to 12 carbon atoms or a monocyclic or polycyclic aromatic or heteroaromatic radical and the ring A is a benzene or naphthalene ring which is unsubstituted or monosubstituted or polysubstituted by halogen, lower alkyl, lower alkoxy or lower alkoxycarbonyl, and the ring B is an aromatic or heteroaromatic radical which has 6 ring atoms and which can contain an aromatic fused ring, it being possible for both the ring B and the fused ring to be substituted.

The ring A is advantageously a benzene nucleus which is unsubstituted or substituted by halogen or lower alkyl. An unsubstituted benzene nucleus is particularly preferred.

As a 6-membered aromatic ring, B is preferably a benzene ring which is unsubstituted or substituted by halogen, cyano, nitro, lower alkyl, lower alkoxy, lower alkylthio, lower alkylcarbonyl, lower alkoxycarbonyl, amino, lower alkylamino, di-lower alkylamino or lower alkylcarbonylamino. As a 6-membered heterocyclic ring B is, in particular, a nitrogen-containing heterocyclic structure of aromatic character, for example a pyridine or pyrazine ring. The ring B can also contain a fused aromatic ring, preferably a benzene ring, and is thus, for example, a naphthalene, quinoline or quinoxaline ring.

The preferred 6-membered aromatic or heterocyclic radicals represented by B are the 2,3-pyridino, 3,4-pyridino, 2,3-pyrazino, 2,3-quinoxalino, 1,2-naphthalino, 2,3-naphthalino or 1,2-benzo radical which is unsubstituted or substituted by halogen, such as chlorine or bromine, nitro, lower alkyl, lower alkoxy, lower alkylthio or an amino group which can be substituted as defined above, a 1,2-benzo radical which is unsubstituted or substituted by chlorine atoms, lower alkoxy or di-lower alkylamino, especially dimethylamino, being particularly preferred.

In formula (I) the heteroaromatic radical X is appropriately linked via a carbon atom of the heteroring to the central (meso) carbon atom of the phthalide compound.

As a heteroaromatic radical, X is, for example, a thienyl, acridinyl, benzofuranyl, benzothienyl, naphthothienyl or phenothiazinyl radical, but is advantageously a pyrrolyl, indolyl, carbazolyl, julolidinyl, kairolinyl, indolinyl, dihydroquinolinyl or tetrahydroquinolinyl radical.

The mononuclear or polynuclear heteroaromatic radical can be monosubstituted or polysubstituted in the ring. Examples of suitable C-substituents are halogen, hydroxyl, cyano, nitro, lower alkyl, lower alkoxy, lower alkylthio, lower alkoxycarbonyl, acyl having 1 to 8 carbon atoms, preferably lower alkylcarbonyl, amino, lower alkylamino, lower alkylcarbonylamino or di-lower alkylamino, $C_5$-$C_6$cycloalkyl, benzyl or phenyl, while examples of N-substituents are $C_1$-$C_{12}$alkyl, $C_2$-$C_{12}$alkenyl, $C_5$-$C_{10}$cycloalkyl, $C_1$-$C_8$acyl, phenyl, benzyl, phenethyl or phenisopropyl each of which can be substituted by, for example, cyano, halogen, nitro, hydroxyl, lower alkyl, lower alkoxy, lower alkylamino or lower alkoxycarbonyl.

The alkyl and alkenyl radicals can be linear or branched. Examples of these are methyl, ethyl, n-propyl, isopropyl, n-butyl, 1-methylbutyl, t-butyl, sec-butyl, amyl, isopentyl, n-hexyl, 2-ethylhexyl, isooctyl, n-octyl, 1,1,3,3-tetramethylbutyl, nonyl, isononyl, 3-ethylheptyl, decyl or n-dodecyl or vinyl, allyl, 2-methallyl, 2-ethylallyl, 2-butenyl or octenyl, respectively.

Preferred heteroaromatic radicals are substituted 2-pyrrolyl or 3-pyrrolyl or especially 3-indolyl radicals, for example N-$C_1$-$C_8$alkylpyrrol-2-yl, N-phenylpyrrol-3-yl, N-$C_1$-$C_8$alkyl-2-methylindol-3-yl, N-$C_2$-$C_4$alkanoyl-2-methylindol-3-yl, 2-phenylindol-3-yl or N-$C_1$-$C_8$alkyl-2-phenylindol-3-yl radicals.

As an aromatic radical, X can be a phenyl or naphthyl radical which is unsubstituted or substituted by halogen, cyano, lower alkyl, $C_5$-$C_6$cycloalkyl, $C_1$-$C_8$acyl, —$NR_1R_2$, —$OR_3$ or —$SR_3$.

As an aromatic radical, X is preferably a substituted phenyl radical of the formula

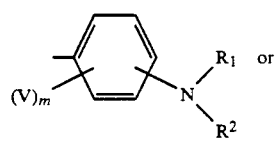
(Ia)

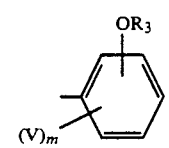
(Ib)

In these formulae $R_1$, $R_2$ and $R_3$ independently of one another are each hydrogen, alkyl which has not more than 12 carbon atoms and is unsubstituted or substituted by halogen, hydroxyl, cyano or lower alkoxy, acyl having 1 to 8 carbon atoms, cycloalkyl having 5 to 10 carbon atoms or phenalkyl or phenyl each of which is unsubstituted or substituted in the ring by halogen, trifluoromethyl, cyano, lower alkyl, lower alkoxy, lower alkoxycarbonyl, —NX'X" or X'X"N-phenylamino in which X' and X" independently of one another are hydrogen, lower alkyl, cyclohexyl, benzyl or phenyl, or $R_1$ and $R_2$, together with the nitrogen atom linking them, form a 5-membered or 6-membered, preferably saturated, heterocyclic radical. V is hydrogen, halogen, lower alkyl, $C_1-C_{12}$alkoxy, $C_1-C_{12}$acyloxy, benzyl, phenyl, benzyloxy, phenoxy, benzyl or benzyloxy each of which is substituted by halogen, cyano, lower alkyl or lower alkoxy, or the group $-NT_1T_2$. $T_1$ and $T_2$ independently of one another are each hydrogen, lower alkyl, $C_5-C_{10}$cycloalkyl, benzyl which is unsubstituted or substituted by halogen, cyano, lower alkyl or lower alkoxy, or acyl having 1 to 8 carbon atoms, and $T_1$ is also phenyl which is unsubstituted or substituted by halogen, cyano, lower alkyl or lower alkoxy. m is 1 or 2. $-NR_1R_2$ and $-OR_3$ are preferably located in the para-position relative to the point of attachment. One V is preferably in the ortho-position relative to the point of attachment.

As alkyl, R, X, $R_1$, $R_2$ and $R_3$ are, for example, the substituents enumerated above for alkyl radicals.

If the alkyl radicals in R, $R_1$, $R_2$ and $R_3$ are substituted, they are especially cyanoalkyl, halogenoalkyl, hydroxyalkyl or alkoxyalkyl, each preferably having a total of 2 to 8 carbon atoms, for example 2-cyanoethyl, 2-chloroethyl, 2-hydroxyethyl, 2-methoxyethyl, 2-ethoxyethyl, 2,3-dihydroxypropyl, 2-hydroxy-3-chloropropyl, 3-methoxypropyl, 4-methoxybutyl or 4-propoxybutyl.

Examples of R, $R_1$, $R_2$, $R_3$, $T_1$ and $T_2$ as cycloalkyl are cyclopentyl, cycloheptyl or, preferably, cyclohexyl. The cycloalkyl radicals can contain one or more $C_1-C_4$alkyl radicals, preferably methyl groups, and contain a total of 5 to 10 carbon atoms.

As aralkyl or phenalkyl, R, $R_1$, $R_2$ and $R_3$ can be phenethyl, phenylisopropyl or especially benzyl.

Examples of preferred substituents in the phenalkyl and phenyl group of the R radicals are halogen, cyano, methyl, trifluoromethyl, methoxy or carbomethoxy. Examples of araliphatic or aromatic radicals of this type are methylbenzyl, 2,4-dimethylbenzyl, 2,5-dimethylbenzyl, chlorobenzyl, dichlorobenzyl, cyanobenzyl, tolyl, xylyl, chlorophenyl, methoxyphenyl, 2,6-dimethylphenyl, trifluoromethylphenyl or carbomethoxyphenyl.

The acyloxy radical in V is, for example, formyloxy, lower alkylcarbonyloxy, for example acetoxy or propionyloxy, or benzoloxy. As a $C_1-C_{12}$alkoxy radical, V can be a linear or branched group, for example methoxy, ethoxy, isopropoxy, n-butoxy, tert-butoxy, amyloxy, 1,1,3,3-tetramethylbutoxy, n-hexyloxy, n-octyloxy or dodecyloxy.

If the ($R_1$ and $R_2$) pair of substituents, together with the common nitrogen atom, is a heterocyclic radical, the latter is, for example, pyrrolidino, piperidino, pipecolino, morpholino, thiomorpholino, piperazino, N-alkylpiperazino, for example N-methylpiperazino, N-phenylpiperazino or N-alkylimidazolino. Preferred saturated heterocyclic radicals for $-NR_1R_2$ are pyrrolidino, piperidino or morpholino.

The substituents $R_1$ and $R_2$ are preferably cyclohexyl, benzyl, phenethyl, cyano-lower alkyl, for example β-cyanoethyl, or primarily lower alkyl, for example methyl or ethyl. $-NR_1R_2$ is preferably also pyrrolidinyl. $R_3$ is preferably lower alkyl or benzyl.

V can advantageously be hydrogen, halogen, lower alkyl, for example methyl, benzyloxy, $C_1-C_8$alkoxy, primarily lower alkoxy, for example methoxy, ethoxy, isopropoxy or tert-butoxy, or the group $-NT_1T_2$ in which one of the radicals $T_1$ and $T_2$ is preferably $C_1-C_8$acyl or lower alkyl and the other is hydrogen or lower alkyl. In this case the acyl radical is especially lower alkylcarbonyl, for example acetyl or propionyl. V is preferably acetylamino, dimethylamino, diethylamino, benzyloxy or, especially, lower alkoxy and, particularly, ethoxy or hydrogen.

The substituent X is preferably hydrogen, an N-$C_1-C_8$alkyl-2-methylindol-3-yl radical, an N-$C_1-C_8$alkyl-2-phenylindol-3-yl radical or a substituted phenyl radical of the formula (1a) or (1b).

As a heterocyclic radical, R in formula (1) is primarily a 5-membered or 6-membered heterocyclic structure of aromatic character, preferably containing oxygen, sulfur or nitrogen. Examples of heterocyclic structures of this type are thienyl, furyl, pyrrolyl, pyrazolyl, imidazolyl or pyridyl radicals.

R can also be a multinuclear heterocyclic ring system. This preferably contains a fused benzene or naphthalene ring, for example a substituted or unsubstituted benzothiophene, indolyl, benzothiazolyl, coumarin, quinoline or carbazolyl radical. The mononuclear or multinuclear heterocyclic radicals can be substituted, in particular by halogen, hydroxyl, cyano, nitro, lower alkyl, lower alkoxy or lower alkoxycarbonyl. Preferred heterocyclic radicals represented by R are 2-furyl, 2-thienyl, 2-, 3- or 4-pyridyl or 5-lower alkoxycarbonyl-2-thienyl, for example 5-carbomethoxy-2-thienyl.

R is preferably lower alkyl, especially methyl, or phenyl. Together with R', R is, for example, 1,2-ethylene, 1,2-propylene, 1,3-propylene or 2-methyl-1,3-propylene. The 1,3-propylene radical is preferred.

Lower alkyl, lower alkoxy and lower alkylthio are groups or constituents of groups containing 1 to 6, in particular 1 to 4, carbon atoms. Examples of groups of this type are methyl, ethyl, n-propyl, isopropyl, n-butyl, sec-butyl, amyl, isoamyl or hexyl and methoxy, ethoxy, isopropoxy, isobutoxy, tert-butoxy or amyloxy and methylthio, ethylthio, propylthio or butylthio, respectively.

Halogen is, for example, fluorine, bromine or, preferably, chlorine.

"Acyl" is especially formyl, lower alkylcarbonyl, for example acetyl or propionyl, or benzoyl. Other acyl radicals can be lower alkylsulfonyl, for example methylsulfonyl or ethylsulfonyl, and phenylsulfonyl. Benzoyl and phenylsulfonyl can be substituted by halogen, methyl, methoxy or ethoxy.

Pyran-containing phthalides which are particularly important have the formula

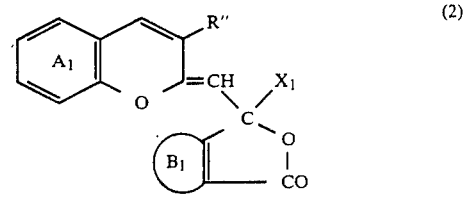

(2)

in which
the ring $A_1$ is unsubstituted or substituted by halogen, lower alkyl or lower alkoxy and the ring $B_1$ is a benzene or pyridine ring which is unsubstituted or substituted by halogen, cyano, lower alkyl, lower alkoxy, lower alkylcarbonylamino or di-lower alkylamino, R'' is lower alkyl, phenyl or phenyl which is substituted by halogen, lower alkyl or lower alkoxy, $X_1$ is hydrogen, a 3-indolyl radical of the formula a substituted phenyl radical of the formula

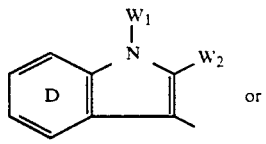
(2a)

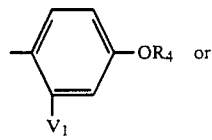
(2b)

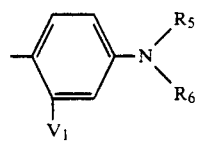
(2c)

in which $W_1$ is hydrogen or $C_1$-$C_8$alkyl which is unsubstituted or substituted by cyano or lower alkoxy or is acetyl, propionyl or benzyl, $W_2$ is hydrogen, lower alkyl, especially methyl, or phenyl, $R_4$, $R_5$ and $R_6$ independently of one another are each alkyl which has not more than 12 carbon atoms and is unsubstituted or substituted by hydroxyl, cyano or lower alkoxy, or are $C_5$-$C_6$cycloalkyl, benzyl, phenethyl or phenyl, or ($R_5$ and $R_6$), together with the nitrogen atom linking them, are pyrrolidino, piperidino or morpholino, $V_1$ is hydrogen, halogen, lower alkyl, $C_1$-$C_8$alkoxy, benzyloxy or the group —$NT_3T_4$, $T_3$ and $T_4$ independently of one another are each hydrogen, lower alkyl, lower alkylcarbonyl or benzoyl which is unsubstituted or substituted by halogen, methyl or methoxy, and the ring D is unsubstituted or substituted by halogen or lower alkyl, such as methyl or isopropyl, or by di-lower alkylamino, such as dimethylamino.

Amongst the phthalide compounds of the formula (2) preference attaches to those in which $X_1$ is hydrogen, a 3-indolyl radical of the formula (2a) in which $W_1$ is $C_1$-$C_8$alkyl and $W_2$ is methyl or phenyl, or a phenyl radical of the formula (2b) in which $R_4$ is lower alkyl and $V_1$ is hydrogen and the ring $B_1$ is a benzene ring which is unsubstituted or substituted by lower alkoxy or di-lower alkylamino. $X_1$ is preferably also 4-di-lower alkylaminophenyl.

Pyran-containing phthalide compounds of particular interest are those of the formula

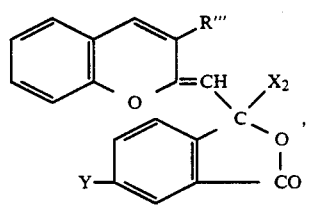
(3)

in which

R''' is lower alkyl, especially methyl or phenyl, $X_2$ is hydrogen, 1-$C_1$-$C_8$alkyl-2-methylindol-3-yl, 4-di-lower alkylaminophenyl or 4-lower alkoxyphenyl and Y is hydrogen, lower alkoxy or di-lower alkylamino, in particular dimethylamino.

Compounds, according to the invention, of the formula (1) can be prepared by reacting a pyrylium salt of the formula (4a) or a 1,2,3,4-tetrahydroxanthylium salt of the formula (4b)

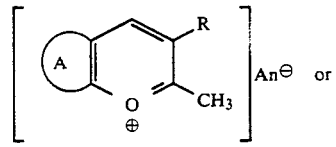
(4a)

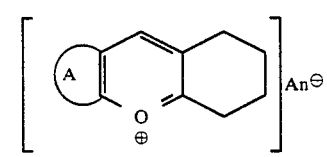
(4b)

in which A and R are as defined above and

An $\ominus$ is an anion, with an aldehyde-acid or keto-acid of the formula

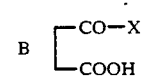
(5)

in which X and B are as defined above.

The reaction is appropriately carried out in organic solvents which are liquid at the reaction temperature, for example carboxylic acids, such as acetic acid, carboxylic anhydrides, such as acetic anhydride, acetonitrile or propionitrile, if desired in the presence of acid or basic condensation agents, for example sulfuric acid, phosphoric acid, phosphorus oxychloride, zinc chloride, toluenesulfonic acid or boric acid, triethylamine, pyridine or piperidine. The condensation is advantageously carried out at temperatures within the range from 20° to 120° C., preferably 40° to 80° C.

The cyclization to give the phthalide can be effected together with the condensation or subsequently to the latter in the same operation or in a separate operation, appropriately in the presence of a base, for example potassium hydroxide or carbonate, sodium hydroxide or carbonate, ammonia, aliphatic amines or pyridine. The end product of the formula (1) is isolated in a generally known manner by separating off the resulting precipitate and washing and drying it or by treating the precipitate with suitable organic solvents, for example methanol, isopropanol, benzene, chlorobenzene or toluene.

Some of the starting materials of the formulae (4a) and (4b) required for the preparation of the pyran-containing phthalides are known.

The pyrylium salts of the formula (4a) and xanthylium salts of the formula (4b) can be employed in the form of their chlorides, tetrachloroferrates, tetrafluoroborates, trichlorozincates, perborates or perchlorates. Trichlorozincates and especially tetrachloroferrates are preferred.

The following are suitable pyrylium salts or xanthylium salts:

2,3-dimethylbenzopyrylium tetrachloroferrate,
2-methyl-3-phenylbenzopyrylium tetrachloroferrate,
2-ethyl-3-phenylbenzopyrylium tetrachloroferrate,
2,3-dimethylbenzopyrylium trichlorozincate,
2-benzyl-3-phenylbenzopyrylium tetrachloroferrate,
2,3-dimethylnaphtho-2,1-b-pyrylium tetrachloroferrate,
2-methyl-3-phenylnaphtho-2,1-b-pyrylium tetrachloroferrate,
2-benzyl-3-phenylnaphtho-2,1-b-pyrylium tetrachloroferrate,
1,2,3,4-tetrahydroxanthylium trichlorozincate and
1,2,3,4-tetrahydrobenzoxanthylium trichlorozincate.

The starting materials of the formula (5) are mostly known. Specific examples include:
5-methoxyphthalaldehydic acid,
5-dimethylaminophthalaldehydic acid,
4'-methoxy-4-dimethylaminobenzophenone-2-carboxylic acid,
4'-diethylaminobenzophenone-2-carboxylic acid,
3-(2'-carboxybenzoyl)-1-ethyl-2-methylindole,
3-(2'-carboxybenzoyl)-1-n-octyl-2-methylindole,
3-(3',4',5',6'-tetrachloro-2'-carboxybenzoyl)-1-ethyl-2-methylindole,
2-(1'-n-octyl-2'-methylindol-3'-yl)-carbonylnicotinic acid and
4,4'-bisdimethylaminobenzophenone-2-carboxylic acid.

The pyran-containing phthalides of the formulae (1) to (3) are normally colourless or, at the most, weakly coloured. When these colour-formers are brought into contact with a, preferably acid, developer, i.e. an electron acceptor, they produce, depending on the meaning of X and the developer used, intense orange, red, violet, green-blue, blue or violet-blue colour shades which are fast to sublimation and light. The phthalides of the formulae (1) to (3) are also very valuable when mixed with one or more other known colour-formers, for example 3,3-(bisaminophenyl)-phthalides, such as CVL, 3-indolyl-3-aminophenylazaphthalides, 3-indolyl-3-aminophenyldiazaphthalides, (3,3-bisindolyl)-phthalides, 3-aminofluorans, 2,6-diaminofluorans, 2,6-diamino-3-methylfluorans, 3,6-bisalkoxyfluorans, 3,6-bis-diarylaminofluorans, leucoauramines, spiropyrans, spirodipyrans, chromenopyrazoles, chromenoindoles, phenoxazines, phenothiazines, quinazolines, rhodamine lactams, carbazolylmethanes or other triarylmethane leuco dyes in order to produce blue, navy blue, grey or black dyeings.

The phthalides of the formulae (1) to (3) exhibit an excellent colour intensity and fastness to light both on activated clays and on phenolic substrates. They are suitable, especially, for use as rapid-developing colour-formers for use in a heat-sensitive or, in particular, pressure-sensitive recording material, which can be either a copying material or a material for new recording. They are distinguished by the fact that they are pH-stable and are excellently soluble in the capsule oils. After exposure to light in a CB sheet they exhibit a slight decrease in colour strength (CB deactivation).

A pressure-sensitive material consists, for example, of at least one pair of sheets containing at least one colour-former of the formulae (1) to (3) dissolved in an organic solvent, and an electron acceptor as developer.

Typical examples of such developers are active clay substances, such as attapulgus clay, acid clay, bentonite, montmorillonite, activated clay, for example acid-activated bentonite or montmorillonite, and also zeolite, halloysite, silicon dioxide, aluminium oxide, aluminium sulfate, aluminium phosphate, zinc chloride, zinc nitrate, zirconium dioxide, activated kaolin or any desired clay. Organic compounds having an acid reaction, for example ring-substituted or unsubstituted phenols, resorcinols, salicylic acids, for example 3,5-bis-($\alpha,\alpha$-dimethylbenzyl)-salicylic acid or 3,5-bis-($\alpha$-methylbenzyl)-salicylic acid, or salicylic acid esters and metal salts thereof, for example zinc salts, as well as a polymeric material having an acid reaction, for example a phenolic polymer, an alkylphenolacetylene resin, a maleic acid/colophony resin or a partially or completely hydrolysed polymer of maleic anhydride with styrene, ethylene or vinyl methyl ether, or carboxymethylene can also be used as developers. It is also possible to employ mixtures of the monomeric and polymeric compounds mentioned. Developers which are particularly preferred are acid-activated bentonite, zinc salicylates or the condensation products of p-substituted phenols with formaldehyde. The latter can also be modified with zinc. The zinc salicylates are described, for example, in EP-A 181,283 or DE-A 2,242,250.

In addition, the developers can also be employed as a mixture with pigments which are unreactive or of low reactivity per se or other adjuncts, such as silica gel or UV absorbers, for example 2-(2'-hydroxyphenyl)-benzotriazoles. The following are examples of such pigments: talc, titanium dioxide, aluminium oxide, aluminium hydroxide, zinc oxide, chalk, clays, such as kaolin, and organic pigments, for example urea/formaldehyde condensates (BET surface area 2-75 $m^2/g$) or melamine/formaldehyde condensation products.

At the points where it comes into contact with the electron acceptor, the colour-former affords a coloured marking. In order to prevent premature activation of the colour-formers present in the pressure-sensitive recording material, as a rule the colour-formers are separated from the electron acceptor. This can be achieved appropriately by incorporating the colour-formers in foam-like, sponge-like or honeycomb-like structures. The colour-formers are preferably enclosed in microcapsules which can, as a rule, be ruptured by pressure.

When the capsules are ruptured by pressure, for example by means of a pencil, the colour-former solution is transferred to an adjacent sheet coated with an electron acceptor, whereby a coloured point is produced. The colour results from the dye which is formed, which has an absorption in the visible range of the electromagnetic spectrum.

The colour-formers are preferably encapsulated in the form of solutions in organic solvents. Examples of suitable solvents are, preferably, non-volatile solvents, for example halogenated paraffin, benzene or biphenyl, such as chloroparaffin, trichlorobenzene, monochlorobiphenyl, dichlorobiphenyl or trichlorobiphenyl, esters, for example tricresyl phosphate, di-n-butyl phthalate, dioctyl phthalate or trichloroethyl phosphate, aromatic ethers, such as benzyl phenyl ether, hydrocarbon oils, such as paraffin or kerosene, aromatic hydrocarbons, for example derivatives of biphenyl, naphthalene or terphenyl which are alkylated by isopropyl, isobutyl, sec-butyl or tert-butyl, dibenzyltoluene, partially hydrogenated terphenyl, mono-$C_1$–$C_3$ alkylated diphenylalkanes to tetra-$C_1$–$C_3$alkylated diphenylalkanes, dodecylbenzene, benzylated xylenes, phenylxylylethane or other chlorinated or hydrogenated, condensed, aromatic hydrocarbons. Mixtures of different solvents, in particular mixtures of paraffin oils or kerosene and diisopropyl naphthalene or partially hydrogenated terphenyl, are often employed in order to obtain an optimal solubility for the colour formation, a rapid and intense coloration and a viscosity advantageous for the micro-encapsulation. In regard to the encapsulation, the phthalides according to the invention are distinguished by the fact that they are readily soluble and exhibit stability to pH, for example within a pH range from 4 to 10.

The capsule walls can be formed uniformly around the droplets of colour-former solution by coacervation forces, the encapsulating material being described, for example, in U.S. Pat. No. 2,800,457. The capsules can preferably also be formed by polycondensation from an aminoplast or modified aminoplasts, as described in British Patent Specifications 989,264, 1,156,725, 1,301,052, 4,100,103 and 1,355,124. Microcapsules formed by interface polymerization, for example capsules formed from polyester, polycarbonate, polysulfonamide, polysulfonate and particularly polyamide or polyurethane, are also suitable.

The microcapsules containing colour-formers of the formulae (1) to (3) can be used for the production of pressure-sensitive copying materials of a very wide range of known types. The various systems differ from one another essentially in the arrangement of the capsules and the colour reactants and in the carrier material.

A preferred arrangement is one in which the encapsulated colour-former is present in the form of a layer on the reverse side of a transfer sheet, and the electron acceptor (colour developer) is present in the form of a layer on the front side of a receiver sheet. Another arrangement of the constituents consists in the microcapsules containing the colour-former, and the developer being present in or on the same sheet in the form of one or more individual layers, or the developer being incorporated in the substrate.

The capsules are preferably fixed on the substrate by means of a suitable binder. Since paper is the preferred substrate, this binder is principally paper coating agents, such as gum arabic, polyvinyl alcohol, hydroxymethylcellulose, casein, methylcellulose, dextrin, starch, starch derivatives or polymer latices. Examples of the latter are butadiene/styrene copolymers or acrylic homopolymers or copolymers.

The paper used is not only normal paper composed of cellulose fibres, but also paper in which the cellulose fibres have been replaced (partly or wholly) by fibres of synthetic polymers. The layer carrier can also be a plastic film.

The duplicating material also preferably consists in containing a capsule-free layer containing the colour-former and a colour-developing layer containing, as the colour developer, at least one inorganic metal salt of a polyvalent metal, especially halides or nitrates, for example zinc chloride, tin chloride, zinc nitrate or mixtures thereof.

The compounds of the formulae (1) to (3) can also be used as colour-formers in a thermoreactive recording material. This contains, as a rule, at least one layer carrier, one or more colour-formers and an electron acceptor and also, if appropriate, a binder and/or wax. If desired, activators or sensitizers can also be present in the recording material.

Thermoreactive recording systems embrace, for example, heat-sensitive recording materials and paper and copying materials and paper. These systems are used, for example, for recording information, for example in electronic calculators, teleprinters, telewriters or recording equipment and measuring instruments, for example electrocardiographs. The production of an image (marking) can also be effected manually by means of a heated pen. Laser beams are another device for producing markings by means of heat.

The thermoreactive recording material can be constructed in such a way that the colour-former is dissolved or dispersed in a binder layer and the developer is dissolved and dispersed in the binder in a second layer. Another possibility consists in dispersing both the colour-former and the developer in one layer. The layer or layers are softened by means of heat in specific areas, whereupon the desired colour is developed immediately in the heated parts.

Suitable developers are the same electron acceptors as are used in pressure-sensitive papers. Examples of developers are the clay minerals and phenolic resins already mentioned or phenolic compounds such as are described, for example, in German Patent Specification 1,251,348, for example 4-tert-butylphenol, 4-phenylphenol, methylenebis-(p-phenylphenol), 4-hydroxybiphenyl ether, α-naphthol, β-naphthol, methyl or benzyl 4-hydroxybenzoate, 4-hydroxybiphenyl sulfone, 4'-hydroxy-4-methylbiphenyl sulfone, 4'-hydroxy-4-isopropoxybiphenyl sulfone, 4,4'-cyclohexylidenediphenol, 4,4'-isopropylidenediphenol, 4,4'-isopropylidenebis-(2-methylphenol), an antipyrine complex of zinc thiocyanate, a pyridine complex of zinc thiocyanate, 4,4-bis-(4-hydroxyphenyl)valeric acid, hydroquinone, pyrogallol, phloroglucinol, p-, m- or o-hydroxybenzoic acid, hydroxyphthalic acid, gallic acid, 1-hydroxy-2-naphthoic acid and boric acid or organic, preferably aliphatic dicarboxylic acids, for example tartaric acid, oxalic acid, maleic acid, citric acid, citraconic acid or succinic acid.

It is preferable to use meltable, film-forming binders for the production of the thermoreactive recording material. These binders are normally water-soluble, whereas the phthalides and the developer are sparingly soluble or insoluble in water. The binder should be capable of dispersing and fixing the colour-former and the developer at room temperature.

Under the action of heat, the binder softens or melts, so that the colour-former comes into contact with the developer and a colour can be formed. Examples of binders which are water-soluble or at least swellable in water are hydrophilic polymers, such as polyvinyl alcohol, polyacrylate acid, hydroxyethylcellulose, methylcellulose, carboxymethylcellulose, polyacrylamide, polyvinylpyrrolidone, gelatine, starch or etherified maize starch.

If the colour-former and the developer are present in two separate layers, it is possible to use water-insoluble binders, i.e. binders soluble in non-polar or only weakly polar solvents, for example natural rubber, synthetic rubber, chlorinated rubber, alkyd resins, polystyrene, styrene/butadiene copolymers, polymethyl acrylates, ethylcellulose, nitrocellulose and polyvinylcarbazole. However, the preferred arrangement is that in which the colour-former and the developer are present in a water-soluble binder in one layer.

In order to ensure the stability of the heat-sensitive recording material or the image-density of the developed image, the material can be provided with an additional protective layer. Protective layers of this type consist, as a rule, of water-soluble and/or water-insoluble resins which are conventional polymer materials or aqueous emulsions of these polymer materials.

The thermoreactive layers and resin layers can contain further additives. In order to improve the degree of whiteness, to facilitate the printing of the paper and to prevent the heated pen from sticking, these layers can contain, for example, talc, titanium dioxide, zinc oxide, aluminium hydroxide, calcium carbonate (for example chalk), clays or organic pigments, for example urea/formaldehyde polymers. In order to cause the colour to be formed only within a limited temperature range, it is possible to add substances such as urea, thiourea, diphenylthiourea, acetamide, acetanilide, benzene sulfanilide, stearamide, bis-stearoyl ethylene diamide, phthalic anhydride, metal stearates, for example zinc stearate, phthalonitrile, dimethyl terephthalate, dibenzyl terephthalate or other appropriate meltable products which induce the simultaneous melting of the colour-former and the developer. Thermographic recording materials preferably contain waxes, for example carnauba wax, montan wax, paraffin wax, polyethylene wax, condensates of higher fatty acid amides and formaldehyde, and condensates of higher fatty acids and ethylenediamine.

A further use of the compounds of the formulae (1) to (3) is the preparation of a colour image by means of photocurable microcapsules, such as are described, for example, in German Offenlegungsschrift 3,247,488.

In the following examples, the percentages indicated are by weight, unless stated otherwise.

EXAMPLE 1

1.8 g of 5-methoxyphthalaldehydic acid and 3.56 g of 2,3-dimethylbenzopyrylium tetrachloroferrate in 10 ml of glacial acetic acid are stirred, with the addition of 0.1 ml of concentrated sulfuric acid, for 1 hour at 60° C. When the condensation is complete, the reaction product is cooled, 20 ml of water are added and the mixture is stirred for 30 minutes at room temperature, after which the precipitate is filtered off and stirred in a mixture of 300 ml of water and 7 ml of 10% sodium hydroxide solution. The resulting mixture is extracted with toluene. The toluene phase is separated off, purified with activated charcoal, dried over sodium sulfate and evaporated. The residue is chromatographed over silica gel. This gives 1.44 g of the compound of the formula

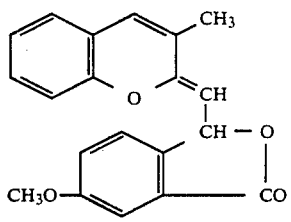

(11)

The melting point of this compound is 97°-99° C. (decomp.). On acid clay, this compound produces a light-fast, red image.

EXAMPLE 2

The procedure of Example 1 is repeated in other respects, except that 1.93 g of 5-dimethylaminophthalaldehydic acid are used instead of 5-methoxyphthalaldehydic acid. This gives 1.47 g of a compound of the formula

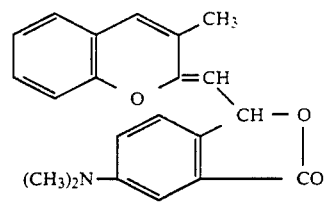

(12)

The melting point of this compound is 141°-142° C. On activated clay, this compound develops a light-fast, blue image.

EXAMPLE 3

2.99 g of 4'-methoxy-4-dimethylaminobenzophenone-2-carboxylic acid and 3.57 g of 2,3-dimethylbenzopyrylium tetrachloroferrate in 20 ml of acetic anhydride are stirred for 7 hours at room temperature. When the condensation is complete, the reaction product is poured onto ice, rendered alkaline with sodium hydroxide solution, treated with toluene and filtered. The phases of the filtrate are separated, after which the organic phase is treated with activated charcoal, dried over sodium sulfate and evaporated. Column chromatography of the residue gives 2.49 g of a compound of the formula

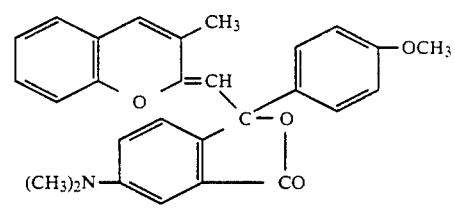

(13)

The melting point of this compound is 112°-113° C. On acid-modified clay, this compound develops a light-fast, grey-blue colour.

EXAMPLE 4

The procedure of Example 3 is repeated in other respects, except that 3.07 g of 3-(2'-carboxybenzoyl)-1-ethyl-2-methylindole are used instead of 4'-methoxy-4-dimethylaminobenzophenone-2-carboxylic acid. This gives a compound of the formula

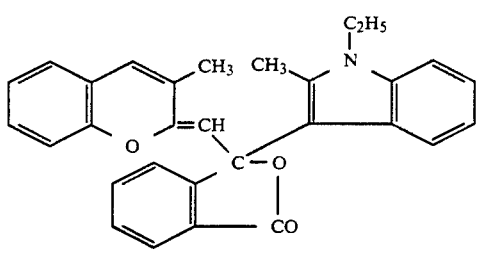

(14)

The melting point of this compound is 193°-195° C. In contact with the acid-modified clay, this compound develops an intense greenish-tinged blue coloration.

Using the corresponding starting materials in the same manner as described in Example 3, phthalides according to the invention of the following formulae are obtained, which have the melting points, and develop the colours, shown below.

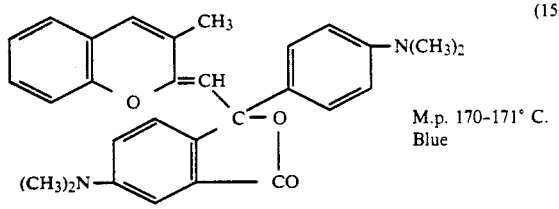
(15) M.p. 170–171° C. Blue

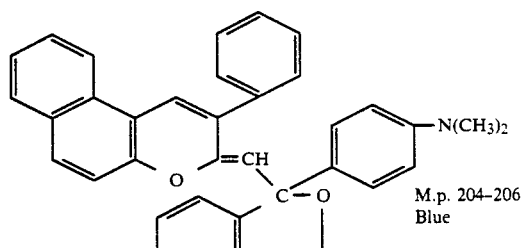
(16) M.p. 204–206° C. Blue

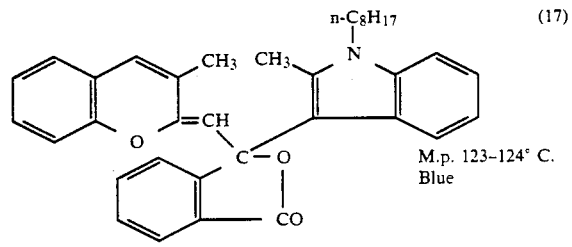
(17) M.p. 123–124° C. Blue

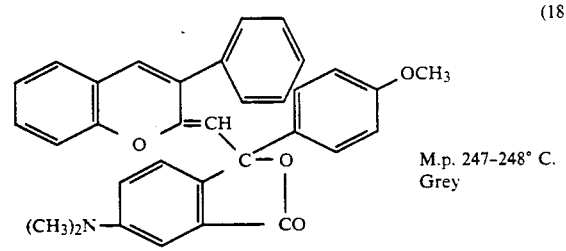
(18) M.p. 247–248° C. Grey

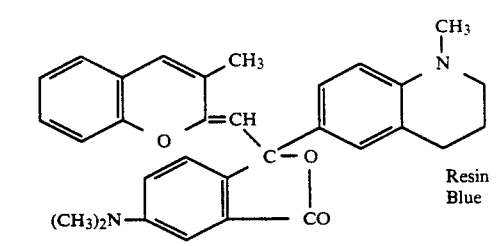
(19) Resin Blue

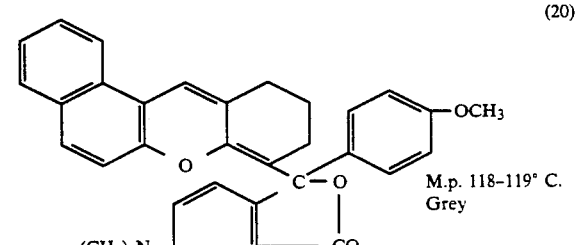
(20) M.p. 118–119° C. Grey

-continued

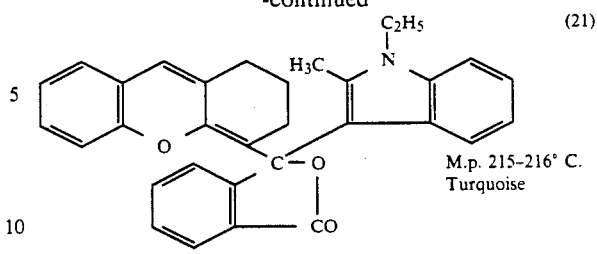
(21) M.p. 215–216° C. Turquoise

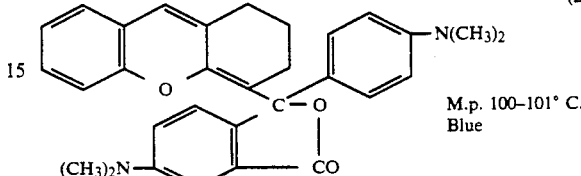
(22) M.p. 100–101° C. Blue

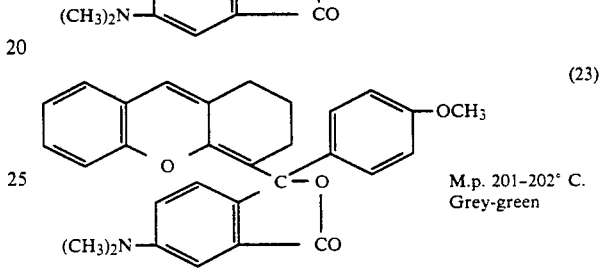
(23) M.p. 201–202° C. Grey-green

EXAMPLE 5

Production of a pressure-sensitive copying paper. A solution of 3 g of the pyran-containing phthalide of the formula (13) (Example 3) in 80 g of diisopropylnaphthalene and 17 g of kerosene is micro-encapsulated by coacervation in a manner known per se, using gelatine and gum arabic, mixed with starch solution and used to coat a sheet of paper. A second sheet of paper is coated on the front side with activated clay as colour developer. The first sheet, containing the colour-former, and the paper coated with colour developer are placed on top of one another with the coatings adjacent. Pressure is exerted on the first sheet by writing with the hand or typewriter, and an intense blue copy which has excellent fastness to light is immediately developed on the sheet coated with the developer.

A corresponding intense, light-fast copy is also achieved if any other of the colour-formers of Examples 1, 2 and 4 indicated in the preparation examples is used.

EXAMPLE 6

1 g of the pyran-containing phthalide of the formula (11) according to Example 1 is dissolved in 17 g of toluene. 12 g of polyvinyl acetate, 8 g of calcium carbonate and 2 g of titanium dioxide are added to this solution, with stirring. The resulting suspension is diluted with toluene in a 1:1 weight ratio and is coated onto a sheet of paper using a 10 μm doctor-blade. A second sheet of paper the underside of which is coated at a coating weight of 3 g/m² with a mixture consisting of 1 part of an amide wax, 1 part of a stearine wax and 1 part of zinc chloride is laid on the first sheet of paper. Pressure is exerted on the upper sheet by writing with the hand or typewriter, and an intense, light-fast, red colour is immediately developed on the sheet coated with the colour-former.

EXAMPLE 7

Production of a heat-sensitive recording material 32 g of 4,4'-isopropylidenediphenol (bisphenol A), 3.8 g of the distearamide of ethylenediamine, 39 g of kaolin, 20 g of an 88% hydrolysed polyvinyl alcohol and 500 ml of water are ground in a ball mill until the particle size is approximately 5 μm. 6 g of the pyran-containing phthalide according to Example 3, 3 g of an 88% hydrolysed polyvinyl alcohol and 60 ml of water are ground in a second ball mill to a particle size of approximately 3 μm.

The two dispersions are combined and used to coat a piece of paper at a dry coating weight of 5.5 g/m². An intense blue colour which has excellent fastness to light and sublimation is obtained by touching the paper with a heated ball-point pen.

Intense and light-fast colours are also obtained if any one of the other colour-formers according to Examples 1, 2 and 4 is used.

EXAMPLE 8

1 g of the colour-former of the formula

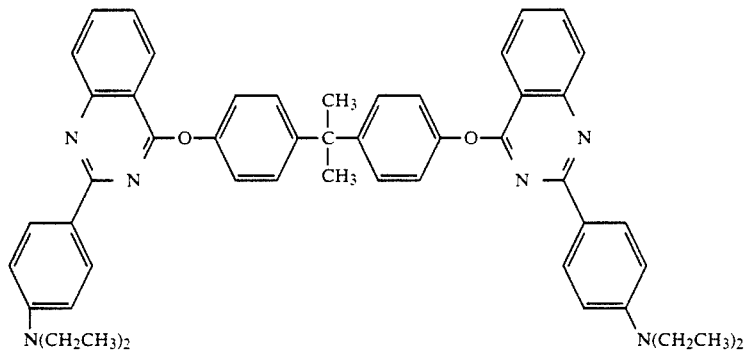

2.65 g of 3,3-bis-(1'-n-octyl-2'-methylindol-3'-yl)-phthalide and 1.35 g of the pyran-containing phthalide of the formula (15) are dissolved at 70°-80° C. in 100 g of partially hydrogenated terphenyl. The cooled solution is applied by means of a gravure printing machine to paper previously sized and coated with activated clay. An intense and light-fast black coloration develops immediately.

What is claimed is:

1. A pyran-containing phthalide of the formula

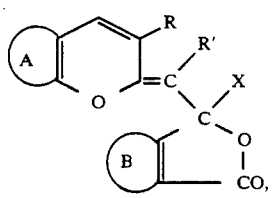

(1)

wherein

R is hydrogen, alkyl which has not more than 12 carbon atoms and is unsubstituted or substituted by halogen, cyano, hydroxyl or lower alkoxy, or is $C_5-C_7$ cycloalkyl or phenyl $C_1-C_3$ alkyl or phenyl each of which is unsubstituted or substituted, by halogen, cyano, methyl, trifluoromethyl, methoxy or carbomethoxy, R' is hydrogen, X is hydrogen, alkyl having 1 to 12 carbon atoms and the ring A is a benzene or naphthalene ring which is unsubstituted or monosubstituted or polysubstituted by halogen, lower alkyl, lower alkoxy or lower alkoxycarbonyl, and the ring B is a hydrocarbyl aromatic radical unsubstituted or substituted by halogen, cyano, nitro, lower alkyl, lower alkoxy, lower alkylthio, lower alkylcarbonyl, lower alkoxycarbonyl, amino, lower alkylamino, di-lower alkylamino or lower alkyl carbonylamino.

2. A phthalide according to claim 1, wherein the ring A in formula (1) is a benzene nucleus which is unsubstituted or substituted by halogen or lower alkyl.

3. A phthalide according to claim 1, wherein the ring B is a substituted or unsubstituted benzene, or naphthalene ring.

4. A phthalide according to claim 1, wherein the ring B in formula (1) is a benzene ring which is unsubstituted or substituted by chlorine, lower alkoxy or di-lower alkylamino.

5. A phthalide according to claim 1, wherein X in formula (1) is hydrogen.

6. A phthalide according to claim 1, wherein R in formula (1) is lower alkyl or phenyl.

7. A phthalide according to claim 1, which has the formula

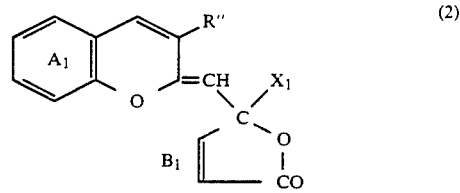

(2)

wherein
the ring $A_1$ is unsubstituted or substituted by halogen, lower alkyl or lower alkoxy and the ring $B_1$ is a benzene ring which is unsubstituted or substituted by halogen, cyano, lower alkyl, lower alkoxy, lower alkylcarbonylamino or di-lower alkylamino, R" is lower alkyl, phenyl or phenyl which is substituted by halogen, lower alkyl or lower alkoxy,
$X_1$ is hydrogen.

8. A phthalide according to claim 1, which has the formula

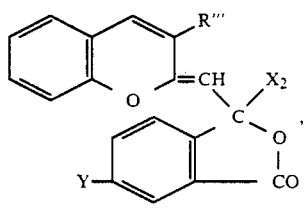
(3)
wherein
R''' is lower alkyl or phenyl,
X₂ is hydrogen, and
Y is hydrogen, lower alkoxy or di-lower alkylamino.
* * * * *
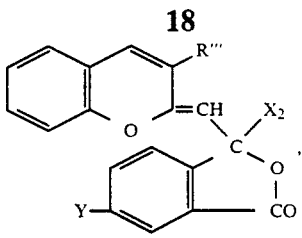
(3)
wherein
R''' is lower alkyl or phenyl,
X₂ is hydrogen, and
Y is hydrogen, lower alkoxy or di-lower alkylamino.
* * * * *